(12) United States Patent
Krivosha et al.

(10) Patent No.: US 6,267,742 B1
(45) Date of Patent: Jul. 31, 2001

(54) BIPLANAR FOOT DORSIFLEXION COLLAPSIBLE POSTERIOR SPLINT

(75) Inventors: Ronald S. Krivosha, Bellevue, WA (US); Ivan E. Brown, Spirit Lake, IA (US)

(73) Assignee: Brown Medical Industries, Spirit Lake, IA (US)

( * ) Notice: Subject to any disclaimer, the term of this patent is extended or adjusted under 35 U.S.C. 154(b) by 0 days.

(21) Appl. No.: 09/162,277

(22) Filed: Sep. 29, 1998

(51) Int. Cl.[7] ................................ A61F 5/00; A61F 5/37; A61F 7/00
(52) U.S. Cl. .................... 602/28; 602/27; 602/2; 128/882; 607/111
(58) Field of Search .................. 602/5–6, 23, 27–29, 602/62, 65, 60–61, 2; 128/882; 607/108, 111–114, 96, 109–110; 5/630, 648–651

(56) References Cited

U.S. PATENT DOCUMENTS

| | | | |
|---|---|---|---|
| 4,572,169 | * | 2/1986 | Mauldin et al. ............... 602/27 |
| 4,646,726 | * | 3/1987 | Westin et al. ................. 602/27 |
| 4,753,229 | * | 6/1988 | Sutherland .................... 602/27 |
| 4,938,222 | * | 7/1990 | Bier, Jr. ..................... 602/27 X |
| 5,067,486 | * | 11/1991 | Hely .......................... 602/27 |
| 5,367,789 | * | 11/1994 | Lamont ........................ 602/28 |
| 5,409,500 | * | 4/1995 | Dyrek ......................... 607/111 |
| 5,415,624 | * | 5/1995 | Williams ...................... 602/21 |
| 5,472,411 | * | 12/1995 | Montag et al. ................. 602/23 |
| 5,486,157 | * | 1/1996 | Di Benedetto .................. 602/27 |
| 5,501,659 | * | 3/1996 | Morris et al. ................. 602/27 |
| 5,591,221 | * | 1/1997 | Owens ......................... 607/111 |
| 5,700,237 | * | 12/1997 | Hess .......................... 602/27 |
| 5,743,867 | * | 4/1998 | Hickling ...................... 602/65 |
| 5,800,490 | * | 9/1998 | Patz et al. ................... 607/108 |
| 5,817,041 | * | 10/1998 | Bader ......................... 602/23 |
| 5,860,423 | * | 1/1999 | Thompson ...................... 128/882 |

FOREIGN PATENT DOCUMENTS

| | | | |
|---|---|---|---|
| 1323103-A | * | 7/1987 | (SU) .......................... 602/28 |
| WO-88000033-A | * | 1/1988 | (WO) .......................... 602/28 |

* cited by examiner

Primary Examiner—Denise Pothier
(74) Attorney, Agent, or Firm—Zarley, McKee, Thomte, Voorhees & Sease

(57) ABSTRACT

A collapsible posterior splint capable of sustained biplanar (frontal and sagittal) dorsiflexion of the foot. The splint is comprised of a compression support sleeve, inserted into a flexible frame, and utilizing adjustable tension straps. This splint is a method of treatment for foot pain, including plantar fasciitis.

7 Claims, 4 Drawing Sheets

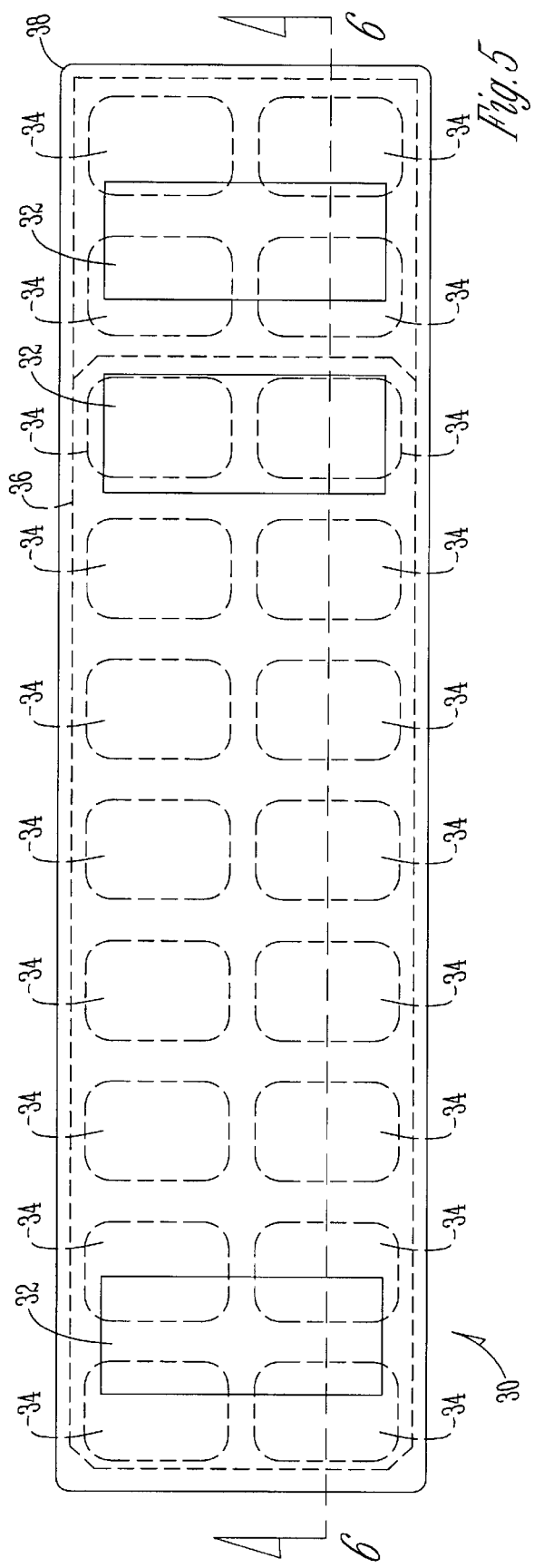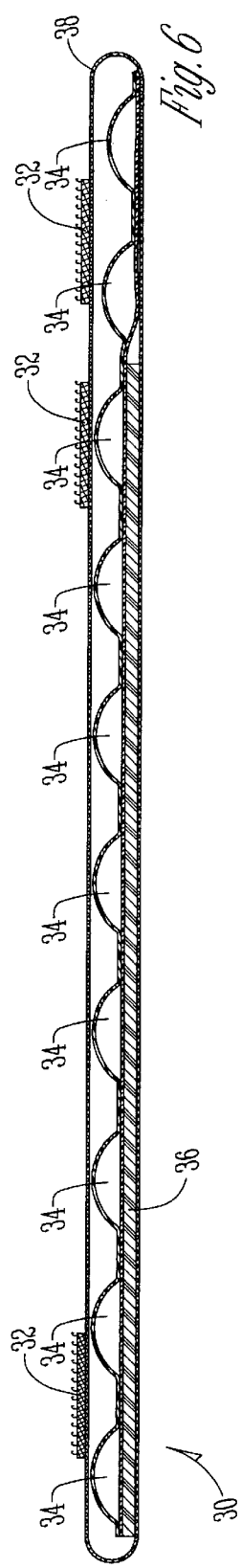

BIPLANAR FOOT DORSIFLEXION COLLAPSIBLE POSTERIOR SPLINT

FIELD OF THE INVENTION

The present invention relates to a collapsible posterior splint capable of sustained biplanar (frontal and sagittal) dorsiflexion of the foot. More particularly, the present invention relates to a splint comprised of a compression support sleeve, inserted into a flexible frame, and utilizing adjustable tension straps.

BACKGROUND OF THE INVENTION

Plantar fasciitis is one of the most common causes of heel pain, which accounts for approximately 15% of all foot-related complaints. This condition occurs in a wide variety of individuals. Commonly, age at onset is in the mid-40's, but plantar fasciitis can develop at any age. Many studies have shown a female-male predominance of 3:1. 65% of patients exhibiting plantar fasciitis are overweight. Approximately 22% of all patients with plantar fasciitis have moderate pronation; about 15% have high-arched, ridge foot; and the remainder have an anatomically normal or non-affected foot. Only 45% of the patients who undergo radiography for suspected plantar fasciitis are found to have a subcalcaneal or "bone" spur.

Evidence of the need for effective therapy is apparent when it is considered that over 95% of all heel pain is diagnosed as plantar fasciitis. Plantar fasciitis is best described as an inflammation of the ligament that runs from the heel to the ball of the foot, which helps support the arch. Patients with plantar fasciitis will experience pain, upon standing, on the bottom or inside of their heel. Typically, the pain is worse in the morning when getting out of bed and after resting when standing up.

Typically the primary anatomic cause of plantar fasciitis is some degree of microtrauma and tearing at the site of the Plantar Fascia insertion. These abnormalities, which may also be present at the origin of the Plantar Fascia, result from repetitive trauma and collagen degeneration and angiofibroblastic hyperplasia. Upon physical examination the range of motion of the affected ankle is less than that of the contralateral ankle. By pressing the thumb against the middle of the affected heel, the physician can delineate the area of the Plantar Fascial pain. Pressure similarly applied underneath the calcaneus reveals the area of subcalcaneal pain. The correlation between plantar fasciitis and subcalcaneal spurs is not significant, therefore radiographic findings are not specific. Conservative treatment, including night splints, results in relief of plantar fasciitis in 85% of patients. In 15% of patients in whom this approach fails, surgery is indicated.

One medical method known in the art in reducing Plantar Fascial pain is to stretch the Plantar Fascia for a period of time. By keeping the Plantar Fascia on stretch, it is believed that an ultimate reduction of the internal tension of the Plantar Fascia can be achieved. Through this treatment, it is believed that the pain associated with this medical condition can be reduced, and possibly eliminated.

A typical treatment program would have the patient wear the splint while sleeping, and remove the splint immediately upon awakening in the morning. The patient will continue wearing the night splint for a 3-month period. After that time the patient will be weaned off of the splint in 2-week increments, using the device every other night, then every third night, then every fourth night, and from then on as needed.

A number of plantar fasciitis night splints are known in the art. However, none have the suspension architecture or offer the comfort, ease of use, compactability, or degrees of rotation and angulation of the present device.

By way of illustration of the state of the art, U.S. Pat. No. 4,649,939, issued to R. Curtis on Mar. 17, 1987 utilized over a shoe. U.S. Pat. No. 5,038,762, issued to H. Hess, et. al., on Aug. 13, 1991, teaches of a U-Shaped yoke which can be wrapped about the heel and ankle. U.S. Pat. No. 5,090,404, issued to C. Kallassy on Feb. 25, 1992, teach of another way to place a strap about the heel and foot. U.S. Pat. No. 5,257,969 issued to C. Mance on Nov. 2, 1993 teaches of a foot support which consists of a toe pouch and straps the wrap about the ankle. U.S. Pat. No. 5,425,701 issued to C. Oster et al. on Jun. 20, 1995, teaches of a boot with upright struts which attach to a foot pad designable for each patient's foot shape. U.S. Pat. No. 5,472,411 issued to H. Montag, et. al., on Dec. 5, 1995 teaches of a U-shaped flexible joint collar which wraps about the foot, heel and ankle. U.S. Pat. No. 5,620,413, issued to D. Olson on Jul. 14, 1995 teaches of an ankle brace and wrap comprised of a support sleeve to fit over the foot. U.S. Design Pat. No. Des. 388,174 issued to W. Stano on Dec. 23, 1997 teaches of a ankle brace which wraps about the lower leg, ankle, and foot. U.S. Pat. No. 5,645,525, issued to R. Krivosha on Jul. 8, 1997 teaches of a heel stabilizing device which fits over the foot and heel. While these devices teach of flexible means of foot support, they do not teach a means to keep the foot on stretch which would properly facilitate the treatment indicated for a diagnosis of plantar fasciitis.

U.S. Pat. No. 4,320,748, issued to W. Racette, et al., on Nov. 20, 1980 teaches of a semi-rigid shell which wraps about the leg from the knee below and consists further of a heal plate pivotally connected to said shell. U.S. Pat. No. 4,693,239 issued to W. Clover on Sep. 15, 1987, teaches of a semi-rigid shell similar to the Racette et al. patent, but allows for use in the presence of soft tissue damage. U.S. Pat. No. 5,209,722 issued to J. Mikalus, et al., on May 11, 1993 teaches of an ankle brace consisting of a semi-rigid plates about the leg and a pivotally connected semi rigid foot plate. While these patents teach us of durable means of providing support to the leg, ankle and foot, they do not teach suspension architecture to keep the foot on stretch which would properly facilitate the treatment indicated for a diagnosis of plantar fasciitis.

U.S. Pat. No. 5,603,692, issued to R. Maxwell on Feb. 18, 1997, teaches of a rigid leg support which would keep the foot on stretch at a 90° angle. U.S. Pat. No 5,605,535, issue to J. Lepage on Feb. 25, 1997 teaches of a load bearing foot brace with a pair of splint arms which, in conjunction, will keep the ankle on stretch at a 90° angle. These patents teach of a means to keep the ankle on stretch, however they are limited in the angulation at 90°, lack tension adjustment features, and prove to be uncomfortable to the patient wearing such devices.

U.S. Pat. No. 5,718,673 issued to C. Shipstead on Feb. 17, 1998 teaches of an ankle wrap that is connected to a foot wrap by means which allow for keeping the ankle on stretch at a 90° angle. This teaches a less uncomfortable means to keep the ankle on stretch, but does not provide the degrees of angulation, nor means for applying an ice/cold pack this current invention teaches.

In summary, while night splints have been used in the past for plantar fasciitis, all are deficient in either comfort, suspension architecture, adjustability, or ease of patient use.

OBJECTIVES OF THE INVENTION

A primary objective of this invention is to provide a collapsible posterior splint which overcomes the disadvantages of the prior art devices to allow comfort, ease of patient use, suspension architecture and adjustability.

It is a further objective of this invention to provide a posterior splint capable of sustained biplanar dorsiflexion of the foot in both frontal and saggital directions.

It is still a further objective of this invention to provide a splint that can be used in preventing contracture of soft tissue structures responsible for heel, Achilles tendon fascia and triceps surae pain.

It is a yet further objective of this invention to provide a collapsible posterior splint capable of containing a removable ice/cold pack to further reduce heel and plantar fascia pain, and to provide comfort to further encourage patient compliance.

The method and manner of accomplishing these and other objectives is described below.

SUMMARY OF THE INVENTION

The collapsible posterior splint basically comprises a bottom stabilizing plate to which is attached at its posterior end leg braces, and on the opposite end are attached two straps which can be attached to the leg braces. The leg brace may have an additional attached strap which will provide support about the leg. A soft sleeve for receipt of a patient's foot and designed to surround the foot, ankle and lower leg is inserted and attached within said bottom stabilizing plate and leg brace. Adjustable straps to secure said sleeve around the foot, ankle and leg are placed on said sleeve. An ice/cold pack is designed to be inserted within the interior of said sleeve beneath the foot and beneath and behind the heel. The coaction of these parts in use provides comfort, adjustable suspension architecture and cold pack use all at once.

DESCRIPTION OF THE DRAWINGS

FIG. 5 displays an ice/cold pack constructed in accordance with this invention.

FIG. 6 is a cross sectional view taken along line 6—6 of FIG. 5.

DETAILED DESCRIPTION OF THE PREFERRED EMBODIMENT

Figure 1:
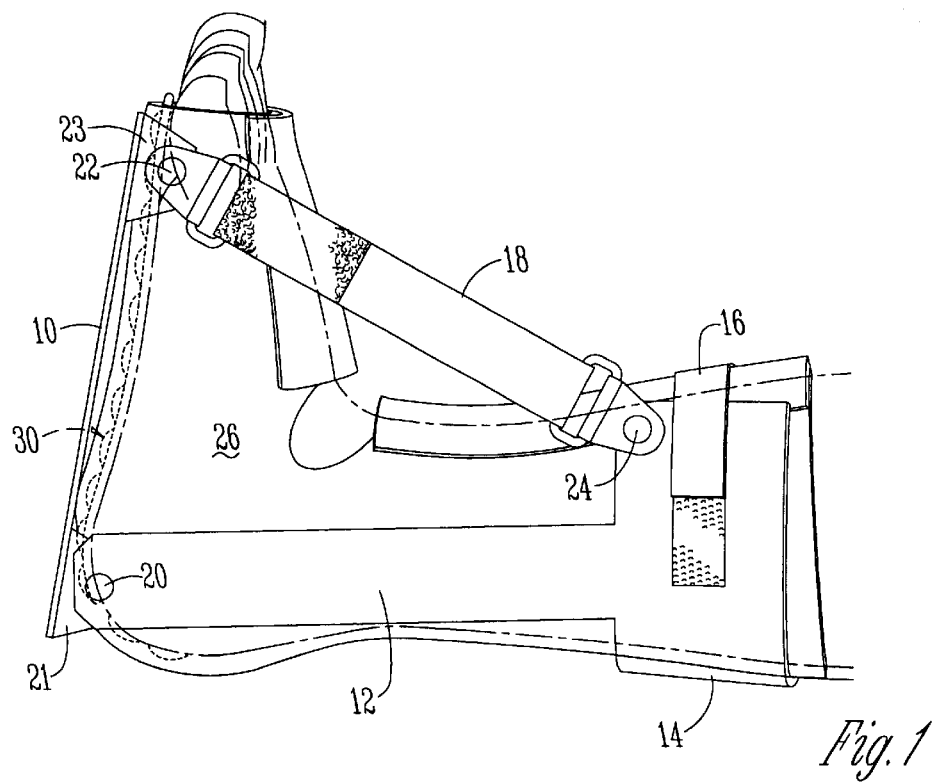
FIG. 1 is an elevated perspective view of an ankle splint constructed in accordance with this invention, and in use.

FIG. 1 shows an improved biplanar foot dorsiflexion collapsible posterior splint in accordance with the present invention. It includes a lightweight, semi-rigid bottom stabilizing plate 10 which has two posterior wings 21 on the medial and lateral sides and two anterior wings 23 21 also on the medial and lateral sides. The posterior wings are pivotally attached at locations 20 to the leg brace 12 in both medial and lateral aspects, providing rotation about pivots 20. At the top of the leg brace 12 is attached a semi-rigid back leg collar 14. Affixed to the back leg support or collar 14 is a front leg strap 16. These means of attachment preferably include thistle cloth or hook and pile fasteners sold under the trademark "Velcro". Adjustable flexion straps 18 are attached anteriorly to the back leg support 14 at pivot connections 24. Adjustable flexion straps 18 are attached to the medial and lateral anterior wings 23 of the stabilizing plate 10 through anterior pivot connections 22. These straps are adjustably through use of thistle cloth or hook and pile fasteners sold under the trademark "Velcro".

Figure 3:
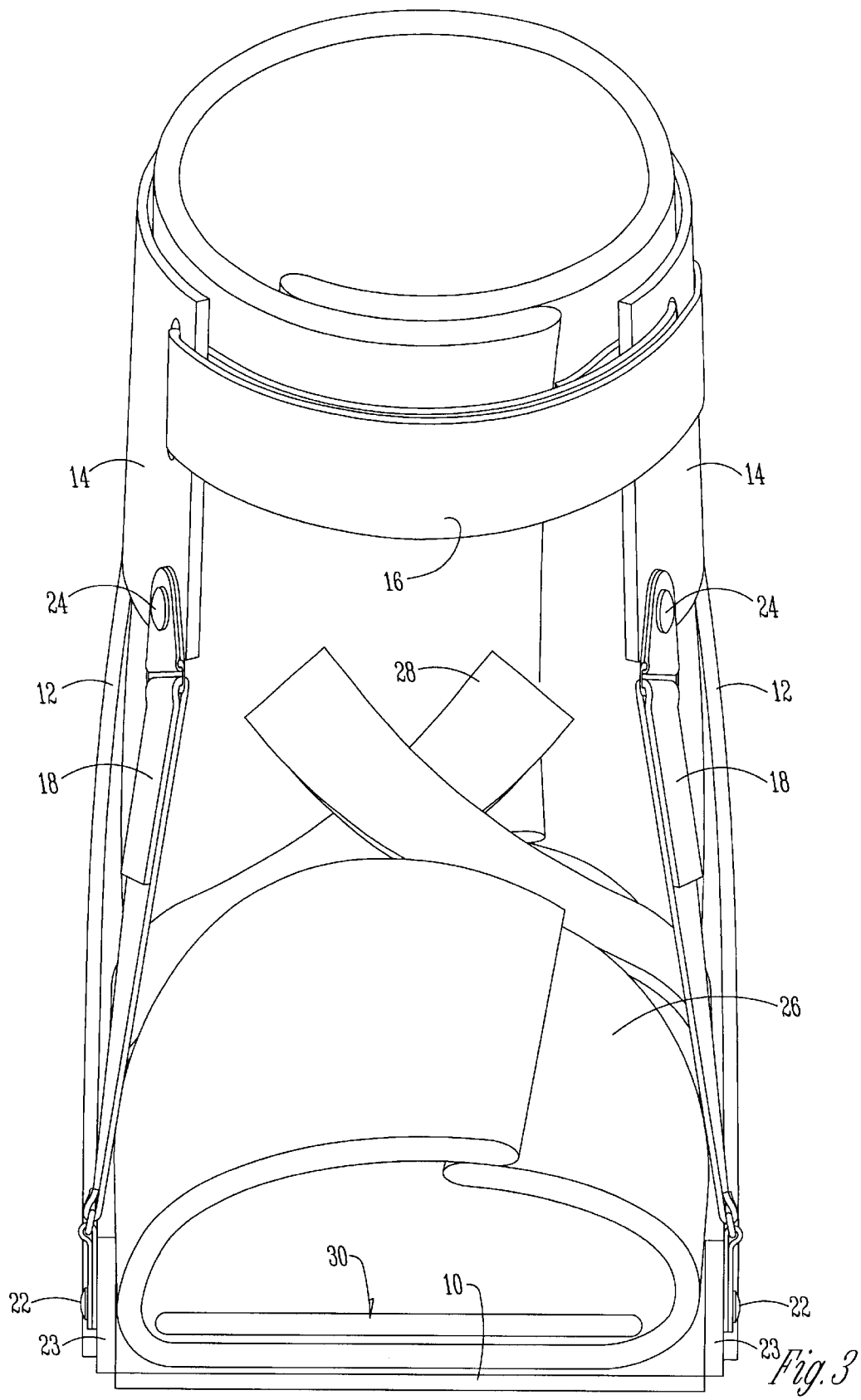
FIG. 3 is a front view of the device of FIG. 1.

A foam sock 26 is made of a soft, durable natural fiber or foamed polymeric material designed to encompass a portion of the foot, the ankle and lower leg. Preferably, the sock is made so that the anterior of the portion which covers the leg and the top of the portion which covers the foot can be opened, adjusted and then closed and secured. Preferably, these means of securing the sock include thistle cloth or hook and pile fasteners sold under the trademark "Velcro". Preferably, additional sock straps 28 are placed to circumnavigate the foot, interior to the heel to provide additional means to secure the sock about the foot (FIG. 3).

An ice/cold pack 30 (FIGS. 5 and 6) can be inserted on the interior portion of the sock to provide contact with the lower foot portion of the heel and also the back of the heel. If desired, ice pack 30 can be a foam pack of identical configuration, except foam replaces the ice. The ice pack 30 comprised of an outer shell 38, preferably made of a durable nylon cloth encasing ice/cold cells 34 and a thin temperature transfer plate 36, preferably made of inert plastic. Transfer plate 36 is placed between the ice/cold cells and the patient's foot to facilitate even transfer of the temperature from the ice/cold cells 34. Adhesion fastener points 32 are affixed on the exterior of the outer shell 38 and are subsequently attached to the inside of the sock 26. Preferably these attachments 32 are also thistle cloth or hook and pile fasteners sold under the trademark "Velcro".

The sock 26 is then inserted into the shell, formed mainly of the bottom stabilizing plate 10, the leg brace 12 and the back leg collar 14. The sock is then attached to said shell by adhesion fasteners 32.

Figure 2:
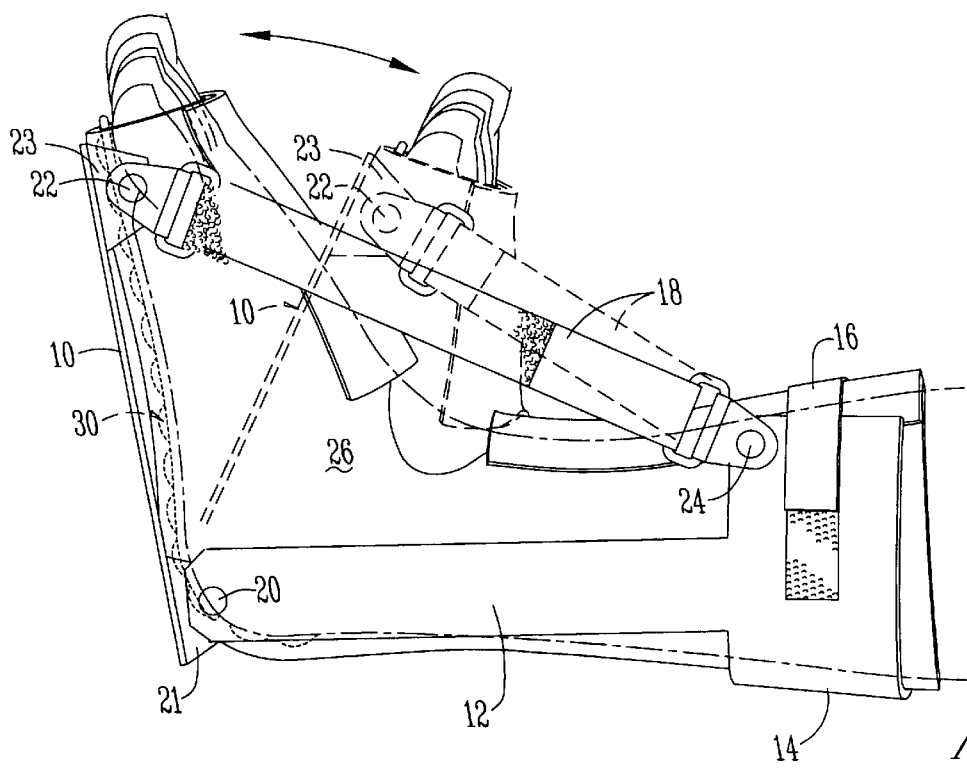
FIG. 2 is an elevated side view of the ankle splint shown in FIG. 1 displaying one possible flexion adjustment of the device.
Figure 4:
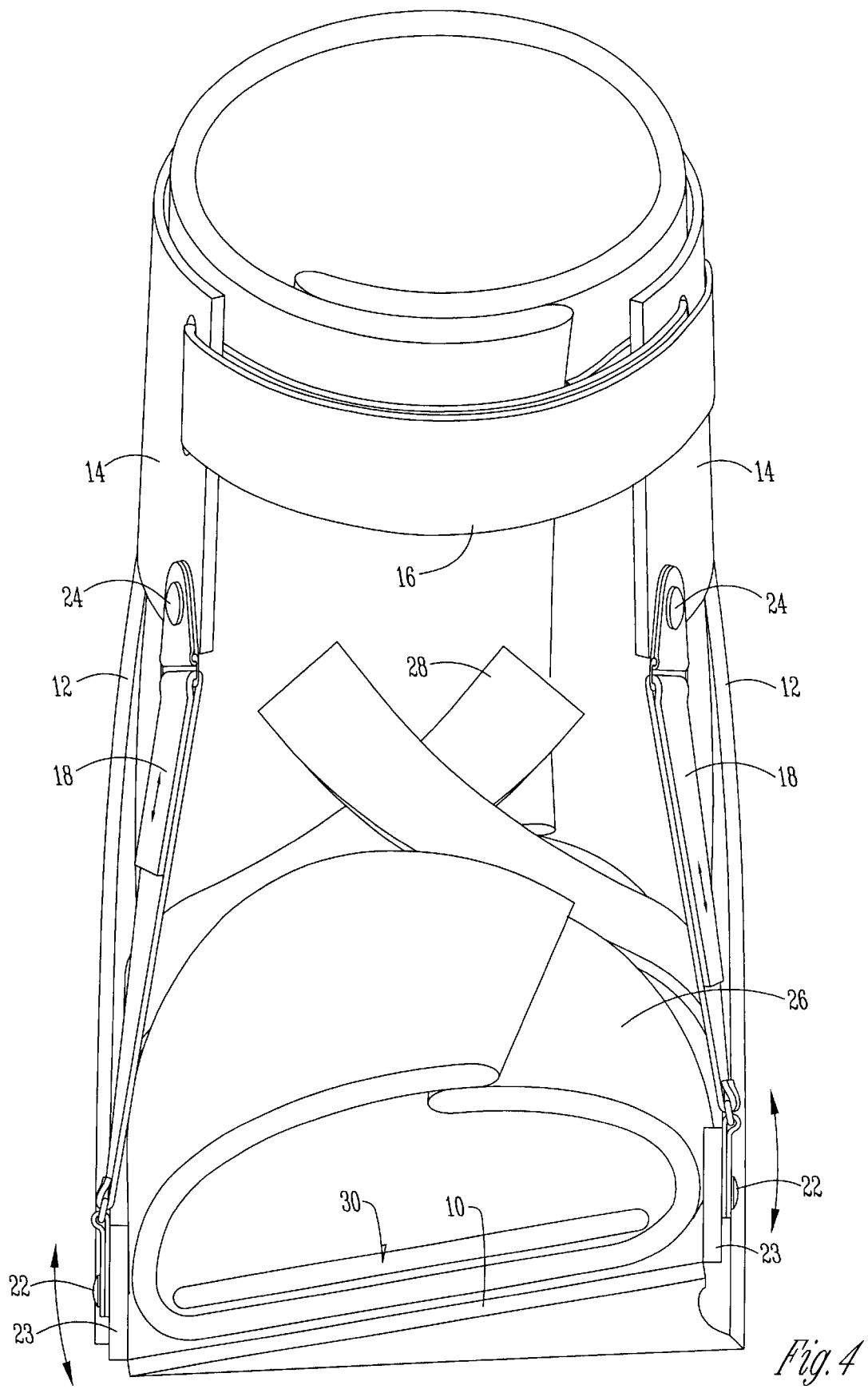
FIG. 4 is also a front view, but displaying the ability of the device to provide biplanar positioning.

In actual operation, the orthopedic splint works as follows. The patient's foot is inserted into sock 26 and then into the shell formed by foot stabilizing plate 10, leg brace 12 and back leg collar 14. Front leg straps 18 can be adjusted to provide an adjustable suspension position of the foot as illustrated in FIGS. 1 and 2. Pronation adjustments of the strap can also be made, see FIGS. 3 and 4. As well, the cold pack 30 can be inserted in sock 26, if desired. Cold pack 30 and sock 26 are optionally used, but are preferred.

What is claimed is:

1. An orthopedic device for adjustable flexion treatment of plantar fascitis, comprising:

a support shell including a support plate having medial and lateral sides, an anterior portion, and a posterior portion, and a pair of support extensions having upper and lower ends, the support plate attached to the support extensions substantially at a side of the posterior portion and at the lower end of the support extensions, one of said extensions attached to the medial side of said support plate and the other of said support extensions to the lateral side of said support plate; said support extensions being connected by a collar adapted to engage a wearer's leg;

medial and lateral adjustable straps, each having one part of said strap attached at the anterior portion of said support shell plate and another part of said strap attached at the upper end of said support extension;

an adjustable leg strap attached at the upper end of said support extension adapted to secure a wearer's leg within the shell; a sock adapted for a foot and insertion into said support shell, the sock including a heat energy transfer pack having barrier layers, said barrier layers encapsulating a material having a high specific heat, said pack further comprises a heat energy transfer plate located between the high specific heat material of the pack and a foot placed in said sock during use.

2. An orthopedic device for adjustable flexion treatment of plantar fascitis, comprising:

a support shell for receiving a patient's foot and lower leg, the shell including a semi-rigid plate for supporting the sole of the patient's foot and first and second upright leg braces attached to the plate;

the plate having opposite first and second sides, a posterior portion, and an anterior portion;

the plate and leg braces creating an unobstructed frontal opening so that the patient can insert the lower leg and foot through the opening and releasably secure the device to the patient;

the first and second upright leg braces each having upper and lower portions, the lower portion of each of the leg braces being pivotally connected to the posterior portion of the plate;

first and second pivot connections mounted on the first and second sides of the anterior portion of the plate respectively;

third and fourth pivot connections mounted on the upper portions of the first and second upright leg braces respectively;

a first tensioning strap spanning between the first and third pivot connections and a second tensioning strap spanning between the second and fourth pivot connections, the first and second tensioning straps being independently adjustable so as to allow pronation adjustments of the straps and thus the plate.

3. The device of claim 2 wherein each of the tensioning straps includes an elongated strip of flexible material having hook and pile fastening means thereon, the strip being adjustably formed into a loop and releasably fastened to itself by said fastening means such that the loop has spans an effective length that is infinitely variable between a first length and a second length.

4. The device of claim 2 wherein first and second posterior wings extend upwardly respectively from the sides of the plate at the posterior portion and the first and second upright leg braces are pivotally attached to the first and second posterior wings respectively.

5. The device of claim 2 wherein first and second anterior wings extend upwardly respectively from the sides of the plate at the anterior portion and the first and second pivotal connections are attached to the first and second anterior wings.

6. The device of claim 2 further comprising a C-shaped leg collar interconnecting the leg braces.

7. The device of claim 6 further comprising a releasably securable and adjustable leg strap on the C-shaped leg collar for securing the patient's lower leg to the device.

* * * * *